United States Patent [19]

Blue

[11] Patent Number: 4,978,521

[45] Date of Patent: Dec. 18, 1990

[54] COLOR CODED FLAVORED DENTIFRICE TOOTHPOWDERS

[76] Inventor: John Duncan Blue, 605 Hama Dr., Holiday, Fla. 34691

[21] Appl. No.: 460,530

[22] Filed: Jan. 3, 1990

[51] Int. Cl.$^5$ .......................... A61K 7/16; A61K 7/18; A61K 9/14

[52] U.S. Cl. ........................ 424/7.1; 424/49; 424/52; 424/57; 424/452; 424/454; 424/465

[58] Field of Search .............................. 424/7.1, 49, 52

[56] References Cited

U.S. PATENT DOCUMENTS

| | | | |
|---|---|---|---|
| 2,015,062 | 9/1935 | Benjamin | 124/7.1 |
| 3,957,964 | 5/1976 | Grimm | 424/49 |
| 4,069,311 | 1/1978 | Mannara | 424/49 |
| 4,069,312 | 1/1978 | Mannara | 424/49 |
| 4,071,614 | 1/1978 | Grimm | 424/49 |
| 4,202,878 | 5/1980 | Ritze | 424/7.1 |
| 4,376,762 | 3/1983 | Hauschild et al. | 424/7.1 |
| 4,376,763 | 3/1983 | Barth et al. | 424/7.1 |
| 4,440,877 | 4/1984 | Hauschild et al. | 424/7.1 |
| 4,663,152 | 5/1987 | Barth et al. | 424/7.1 |

*Primary Examiner*—Shep K. Rose
*Assistant Examiner*—Bart Brooks

[57] ABSTRACT

Dentifrice preparations comprising powder, pellets, capsules and tablets wherein said solutions contain a combination of a selected active fluoride ingredient and optional ingredients selected from the passive group of ingredients comprising plaque, tartar, detergent, sweetner, flavoring, coloring, binding, fast acting with saliva or water and Non-caking agents which form a variety of well balanced, effective and convenient "PORTION CONTROL" toothpowder cleansers.

9 Claims, No Drawings

COLOR CODED FLAVORED DENTIFRICE TOOTHPOWDERS

BACKGROUND OF THE INVENTION

This invention relates to a variety of convenient dentifrice variations which have the effect of totally cleaning teeth and can be easily carried around on a daily basis.

Many different dentifrice preparations are patented for cleaning the oral cavity, both teeth and gums. Each have specific ingredients usually in toothpaste-gel form. These paste-gel forms are available to the consumer in large tubes which are not convenient to carry around in our, on the road, fast pace society of today.

Thus, after reviewing numerous U.S. Patents ranging from U.S.# 1,082,681 through U.S.# 4,547,362 in powder through tablet preparations, the drawbacks become evident.

In U.S. Pat.# 4,547,362(Winston et al) there is too much sodium bicarbonate yielding an unbalanced toothpowder and in U.S. Pat.# 3,116,208(Edmonds Sr.) the toothpowder tablet has NO sodium fluoride and remains in tablet form until it is crushed by the teeth of the user. The active ingredients being calcium carbonate and sodium lauryl sulphate. This tablet is out of date and not effective for today's standard and technology. In U.S. Pat. # 3,151,028(Hay, Schram) the dental tablet is not fast acting but slow release and is an alternative to using a toothbrush on inconvenient occasions.

All of the prior art references have drawbacks from NO fluoride to unbalanced preparations. Most never reach the consumer market because they are only theories and when taken to practice do not yield results claimed. Although the Winston formulation did reach today's market with a tradename of DENTAL CARE TM "The Baking Soda Tooth Powder" from Church & Dwight Co. Inc. Again the base of sodium bicarbonate is strong even with flavoring added.

SUMMARY AND DETAILED DISCLOSURE OF THE INVENTION

In relation to the POWDER preparation, a tooth powder is formulated with an active agent of fluoride along with a passive base of plaque, tartar, detergent, sweetener, flavoring, coloring and non-caking agents combined.

The fluoride agent may be of sodium fluoride or sodium monofluorophosphate, preferably sodium fluoride in the range of 0.22% to 0.25% preferably approximately 0.22% or 1000 parts per millon.

The passive or cosmetic base agents combining with fluoride are plaque abrasives of chalk, calcium carbonate and sodium bicarbonate with the chalk or calcium carbonate additive range of 35% to 70% preferably approximately 60% and sodium bicarbonate range of 10% to 40% preferably approximately 25%. The tartar agents are tetrasodium pyrophosphate with an additive range of 1% to 7% preferably approximately 3½% and disodium pyrophosphate with an additive range of ½% to 5% preferably approximately 2½%. The detergent additive agent is sodium lauryl sulphate with a range of 1% to 10% preferably approximately 3%. The sweetener agents of sodium sacchrin or nutrasweet with an additive range of 0.1% to 0.8% preferably 0.3%. The flavoring agent may vary from spearmint to bubblegum and amaretto to creme de menthe with an additive range of ½% to 2% preferably approximately 1% and the coloring agent may range from a spectrum of colors from white through black. The color will coordinate with the flavor. An example is bubblegum flavor with a pink or light red F.D.&C. coloring dye. The coloring dye may range from a NON-oil to oil base and water soluable to NON-water soluable, preferable an oil base, NON-soluable dye so as the color will not stay in the consumers mouth and will mix consistantly throughout the powder mixture. A NON-caking agent of silica or a phosphate such as tricalcium phosphate may be optionally added in the range of ½% to 3% preferably approximately 2%.

With the above active and passive ingredients formulated, a well balanced toothpowder results. Fluoride to help fight cavities, plaque agents for the mild abrasion to help remove plaque, tartar agents to help remove and fight tartar, detergent to create a foaming cleansing action and to help disperse the other agents throughout the mouth. Into this preparation is added just enough sweetener and flavor to overcome any bitter aftertaste along with various dyes to color coordinate the variety of flavors. A well balanced, tasty and effective cleansing toothpowder.

In relation to the TABLET preparation, a toothpowder tablet is formulated using the same active and passive agents as in the aforementioned toothpowder ingredients. Into this preparation is added a binding agent from the group of phosphates preferably dicalcium phosphate which mixes well with toothpowder ingredients leaving minimum aftertaste and ranges as an additive of 10% to 50% preferably approximately 20%.Also added to this toothpowder preparation is a fast acting agent from a group of glycolates preferably sodium starch glycolate ranging as an additive from ½% to 5% preferably approximately 2%.This agent gives a fast acting factor to the tablet. The tablet when in contact with saliva or water reacts and disperses quicker than normal, aided by the chewing action, and allows the user to immediately brush their teeth or cleanse their mouth.

With this tablet formulation a little more sweetener and flavoring is added to overcome any aftertaste with the addition of phosphate and glycolate. A higher percentage of detergent is also added to help aid the immediate cleansing action. The non-caking additive of silica or tricalcium phosphate is not necessary in formulating the tablet. The following chart shows the % difference between the powder and tablet:

| AGENTS | PREFERRED AGENT | POWDER % | TABLET % |
| --- | --- | --- | --- |
| Fluoride | Sodium Fluoride | .22% | .22% |
| Plaque | Calcium Carbonate | 62.48% | 40.88% |
|  | Sodium Bicarbonate | 25.00% | 25.00% |
| Tartar | Tetrasodium Pyrophosphate | 3.50% | 3.50% |
|  | Disodium Pyrophosphate | 2.50% | 2.50% |
| Detergent | Sodium Lauryl Sulphate | 3.00% | 4.00% |
| Sweetner | Sodium Saccharin | .30% | .40% |
| Flavoring | All Flavors | 1.00% | 1.50% |
| Coloring | Full Spectrum + Non-Soluable + Oil base + a small amt. |  |  |
| Non-Caking | Silica | 2.00% | ∅ |
| Binding | Dicalcium Phosphate | ∅ | 20.00% |
| Fast Acting | Sodium Starch Glycolate | ∅ | 2.00% |

Furthermore in this tablet formulation the plaque agent such as calcium carbonate may also double and aid in binding the tablet together.

Optionally in the tablet structure formulation the aforesaid agents may be pellet-granularized and discreetly colored-coded with a different color from that of it's adjacent components.

In that respect, the consumer can see the different portions. For example, fluoride would be color-coded blue and plaque reducing agents pink. Similiar to a "CONTACT" cold capsule.

In the preparation as tablets either "A"-color coded agents or "B"-solid colored, the ingredients are mixed together into the previously mentioned % ratio's and placed in a tablet pressing machine as a powder. The machine, using a pressure range of 1,500 IBS. to 8,000 IBS preferably approximately 2,000 IBS.,will compress the powder into tablet form. Yielding a water soluable color-coded "A" or a solid colored tablet "B" with a diameter in the range of ¼" to ½" preferably approximately ⅜",a thickness or height of approximately 1/16" to ⅜" preferably approximately ⅛" and a size volume in the range of 200mg. to 500mg. preferably approximately 300mg. When the ingredients aforesaid are used with these dimensions a physically stable is achieved. This tablet will range from a solid colored tablet such as light green for Watermelon or have more than 1 color coded agent being compressed into the tablet, yet still be may be flavored watermelon. As an example it would be a red, white, blue and green tablet wherein the red may represent fluoride agent, blue the plaque agent, green the tartar agent and the balance of the agents combined as the white component.

The tablets mentioned will be packaged 50 to a bottle and sold to the consumer for dental cleanser purposes.

In relation to the CAPSULE wherein the solid colored powder or the color coded pellet-granularized agents are prepared, the toothpowders as aforesaid mentioned may be formulated without the binding and/or fast acting agents and placed in a capsule which is composed of a gelatin outer skin and is water soluable.

CAPSULE "A"- would contain the dentifrice powder in a variety of colors that coordinate with the various flavors such as watermelon with a light green coloring. The consumer wets the toothbrush, pulls apart the capsule(or places in the mouth to disolve) sprinkles the contained toothpowder onto the bristles and brushes their teeth then rinses.

CAPSULE "B"- would contain the same dentifrice ingredients but as color-coded pellet-granularized agents as aforesaid mentioned. The capsule has a see through outer shell so the consumer can see the different but adjacent color-coded agents. Capsule "B" is used in the same manner as capsule "A" for brushing the teeth.

Both capsule A and B will be placed in a convenient bottles and sold to the consumer as a portion controled dental cleanser.

The dentifrice preparations aforementioned are well balanced formulas for total effective cleansing. Regular, thorough brushing (and flossing) with toothpowders whether in powder, pellet, capsule or tablet form will greatly help the consumer fight plaque and tartar. Toothpowders have better cleansing properties because of the higher percentage of abrasive materials. Toothpaste and gels contain a very high percentage content of thickners and water absorbing-retention agents which are non-cleansers. Toothpowders are easier to formulate than pastes and gels because the ingredients used in toothpowder are stable, compatible and consistantly easy to mix together. These qualities make manufacturing a variety of "portion control" single use toothpowder cleansers easier. As an example, a 300mg. toothpowder tablet can be effectly formulated, within the scope of the aforementioned preparations, to cleanse the consumers teeth.

The CONSUMER REPORTS in Mar. 1986 pages 144 through 152 quote "Taste turns out to be important to everyone, young or old, In our survey, readers named flavor as one of the most important factors in choosing a brand of toothpaste, second only to a toothpaste's ability to fight plaque."

This invention yields the following "PORTION CONTROL" dentifrice preparations;

(1) -Powder - solid colored into bottles.

(2) -Powder - solid colored into gelatin capsules.

(3) -Powder - color-coded pellets into gelatin capsules.

(4) -Powder - color-coded pellets pressed into tablets.

(5) -Powder - solid colored pressed into tablets.

With this invention of dentifrice preparations for cleaning teeth here described it should be understood that various changes may be made in proportions of the agents, arrangement and form without departing from the scope of the following claims. An exclusive property or privilege is claimed as hereby defined.

What is claimed is:

1. A color-coded and flavored dentifrice preparation wherein the dentifrice type is toothpowder selected from a group of color coded ingredients with each color-coded ingredient coordinated with its own flavor comprising an active ingredient of fluoride and mixtures thereof with ingredients selected from the group of ingredients comprising abrasive plaque, tartar, detergent, sweetener, coloring, flavoring non-caking and binding agents.

2. A dentifrice preparation as claimed in claim 1 wherein the active fluoride ingredient is selected from the group of sodium flouride or sodium monofluorophosphate in the amount of 0.20% to 0.25% by weight.

3. A dentifrice preparation as claimed in claim 1 wherein the abrasive plaque agents comprise calcium carbonate between 35% to 70% and sodium bicarbonate between 10% to 40% by weight.

4. A dentifrice preparation as claimed in claim 1 wherein the tartar agents comprise tetrasodium pyrophosphate between 1% to 7% and disodium pyrophosphate between ½% to 5% by weight.

5. A dentifrice preparation as claimed in claim 1 wherein the detergent agent is sodium lauryl sulphate between 1% to 10% by weight.

6. A dentifrice preparation as claimed in claim 1 wherein the sweetener is sodium saccharin between 0.1% to 0.8% by weight.

7. A dentifrice preparation as claimed in claim 1 wherein the flavorings are selected from a group of flavors comprising bubblegum, watermelon, and creme de menthe between ½% to 3% by weight.

8. A dentifrice preparation as claimed in claim 1 wherein color includes coloring dyes comprising the primary colors which coordinate with the flavors and which are NON-water soluble and are oil based.

9. A dentifrice preparation as claimed in claim 1 wherein the NON-caking agent comprises silica or tricalcium phosphate between ½% to 3% by weight.

* * * * *